United States Patent [19]

Berry et al.

[11] Patent Number: 5,125,902
[45] Date of Patent: Jun. 30, 1992

[54] SHEATH/OBTURATOR TO FACILITATE INSERTION OF MEDICAL DEVICES INTO A PATIENT'S VENOUS SYSTEM

[75] Inventors: Gaylord L. Berry, Salt Lake City; J. D. Mortensen, Sandy; Mitchell D. Baldwin; Larry D. Rigby, both of Salt Lake City, all of Utah

[73] Assignee: CardioPulmonics, Inc., Salt Lake City, Utah

[21] Appl. No.: 488,285

[22] Filed: Mar. 2, 1990

[51] Int. Cl.$^5$ ............................................. A61M 5/178
[52] U.S. Cl. ..................................... 604/164; 604/264
[58] Field of Search ............... 604/164, 165, 166, 167, 604/169, 170, 280, 264

[56] References Cited

U.S. PATENT DOCUMENTS

| | | | |
|---|---|---|---|
| 3,633,579 | 1/1972 | Alley et al. | 604/164 |
| 4,205,675 | 6/1980 | Vaillancourt | 604/164 |
| 4,565,544 | 1/1986 | Muller et al. | 604/164 |
| 4,684,369 | 8/1987 | Wildemeersch | 604/264 |
| 4,854,330 | 8/1989 | Evans, III et al. | 604/264 |
| 4,869,718 | 9/1989 | Brader | 604/164 |
| 4,961,729 | 10/1990 | Vaillancourt | 604/164 |

FOREIGN PATENT DOCUMENTS 1438805 11/1988 U.S.S.R. .................. 604/169

*Primary Examiner*—Gene Mancene
*Assistant Examiner*—Michael Lynch
*Attorney, Agent, or Firm*—Workman, Nydegger and Jensen

[57] ABSTRACT

A sheath and obturator is provided for facilitating the insertion of certain medical devices into a patient's vascular system, a vein, or venous system and in particular an in vivo extrapulmonary blood gas exchange device having a bundle comprised of a plurality of elongated gas permeable tubes being potted at each end and enclosed within a respective air tight proximal and distal chamber. The sheath is hollow and substantially tubular with a tapered receiving portion and a nontapered, curved entry portion. The obturator has a tip at the distal end of the obturator and a trip at the proximal end with an elongate member therebetween. The sheath is configured to receive the obturator in sliding engagement such that when the obturator is fully inserted within the sheath, the tip closes the opening at the entry end of the sheath and protrudes slightly therefrom. The obturator has a vent which provides a passage from space exterior to the sheath into the hollow interior of the sheath. The sheath and obturator are inserted into the patient through a single incision. Upon removal of the obturator from the sheath, a extrapulmonary blood gas exchange device may be inserted into and through the sheath into one of the right external iliac, common femoral or internal jugular veins, and then into the vena cavae where the elongate gas permeable tubes may be deployed for blood oxygenation.

49 Claims, 3 Drawing Sheets

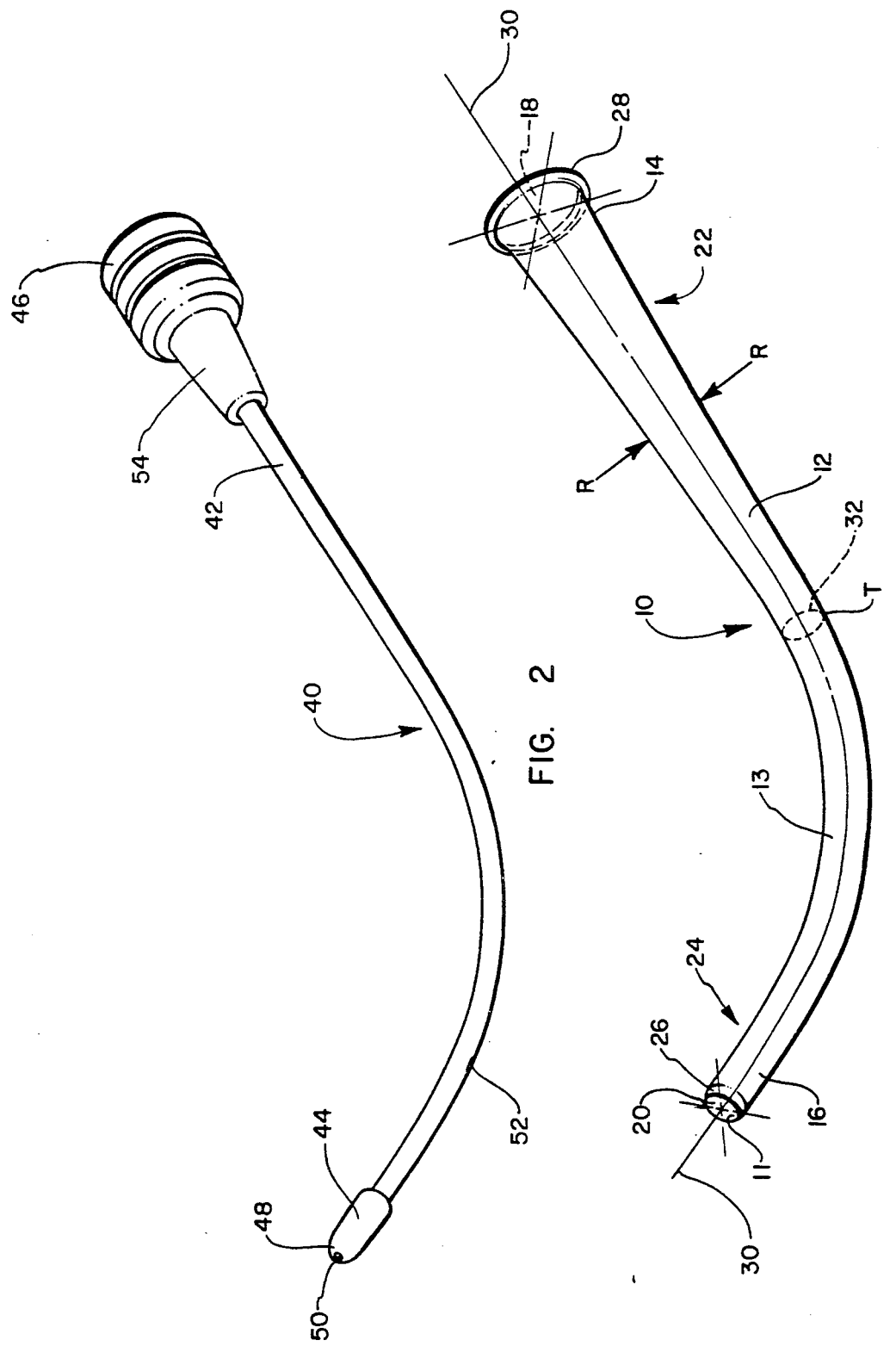

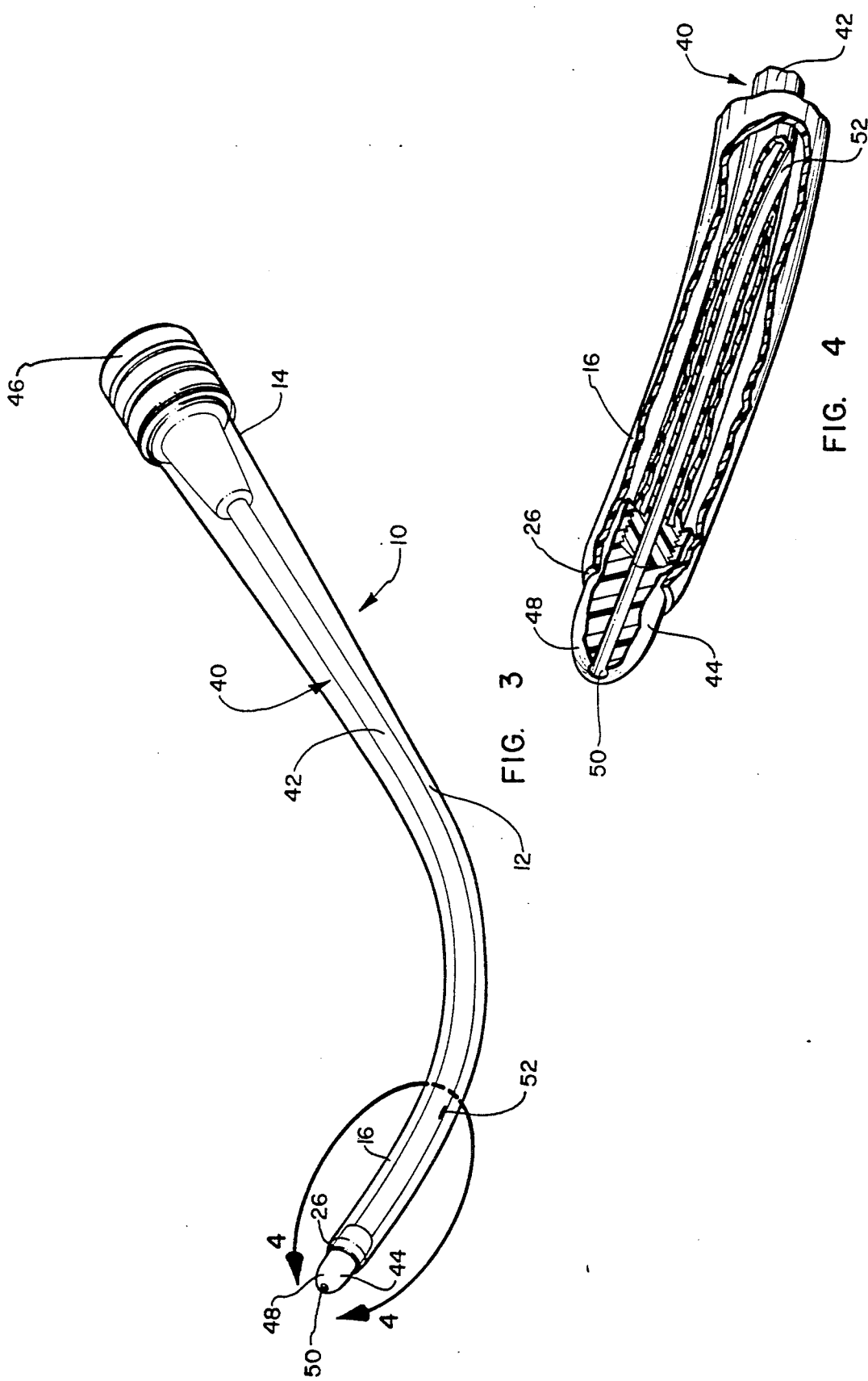

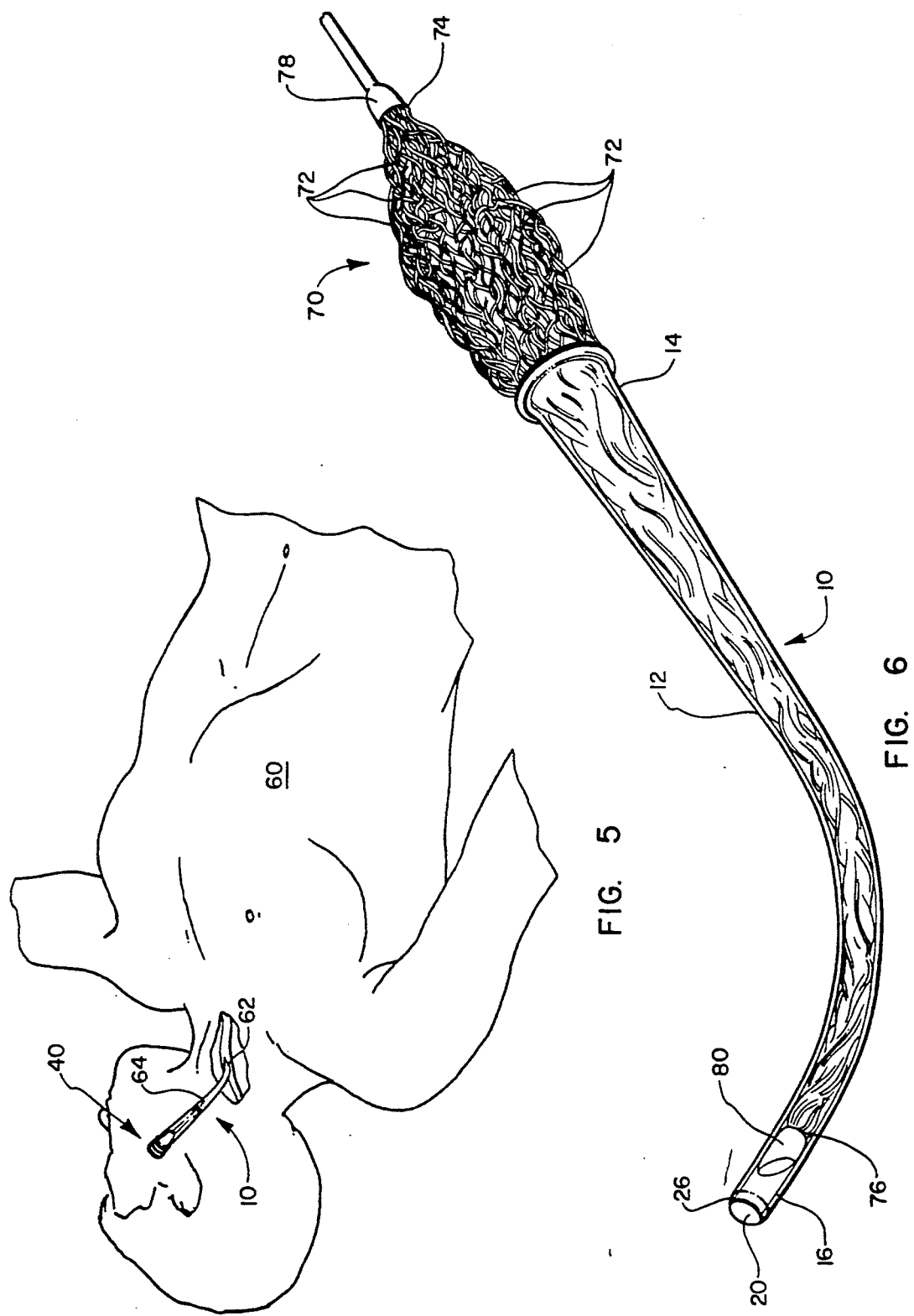

SHEATH/OBTURATOR TO FACILITATE INSERTION OF MEDICAL DEVICES INTO A PATIENT'S VENOUS SYSTEM

BACKGROUND

1. Field of the Invention

The present invention relates to methods and apparatus for introducing medical devices into a patient's venous system (i.e., veins, vascular system, vena cavae, etc.). More particularly, the present invention relates to a method and apparatus for introducing an extrapulmonary blood gas exchange device into a patient's venous system enabling blood to receive oxygen and release carbon dioxide.

2. The Prior Art

Thousands of patients in hospitals suffer from inadequate blood gas exchange, which includes both inadequate blood oxygenation and inadequate removal of carbon dioxide ($CO_2$). These conditions are commonly caused by varying degrees of respiratory inadequacy usually associated with acute lung illnesses such as pneumonitis, atelectasis, fluid in the lung, or obstruction of pulmonary ventilation. Various heart and circulatory ailments such as heart disease and shock can adversely affect the flow of blood and thereby also reduce the rate of blood gas exchange.

Currently the most widely used methods of treating these types of blood gas exchange inadequacies involve increasing the flow of oxygen through the lungs by either increasing the oxygen concentration of the inspired gases or by mechanically ventilating the lungs. Both methods result in placing further strain on the lungs, which may be diseased and unable to function at full capacity. In order to allow diseased or injured organs to heal it is generally best to allow these organs a period of rest followed by a gradual increase in activity. The current methods for treating inadequate blood gas exchange, however, force the diseased or damaged lungs to work even harder rather than allowing them a period of rest and recovery.

Various devices have been developed which are capable, at least for a limited period of time, of taking over the gas exchange function of the lungs. Many extracorporeal blood oxygenators are in common use and are employed most frequently during heart surgery. These devices are capable of providing blood oxygenation sufficient to carry the patient through the surgical procedure. These oxygenators include devices which bubble oxygen into the blood as the blood flows through the device. This is usually followed by a section of the device which defoams the blood to make it acceptable for reinjection into the patient.

Another group of extracorporeal oxygenators employ gas permeable membranes. These devices take many different shapes and configurations; however, the basic concept of operation is the same in all of these devices. Blood flows on one side of the gas permeable membranes while an oxygen rich gas flows on the other side of the membrane. As the blood flows through the device, the oxygen travels across the gas permeable membrane and enters the blood. This allows oxygenation of the blood without actually introducing oxygen bubbles into the blood and without the corresponding need for an extensive defoaming apparatus.

Gas permeable membranes used in such extracorporeal oxygenators are of two types. One type uses a microporous membrane which allows blood gas interface through micropores in the membrane. The other type is a continuous membrane which does not have micropores but which allows blood gas exchange through the membrane without the blood gas interface.

The microporous and bubble oxygenators discussed above are not suited for use outside the setting of a cardiopulmonary bypass procedure, and are thus typically designed for short term extracorporeal use. As a result, these devices are of limited use in the long term intensive care of respiratory failure patients.

In vivo extrapulmonary blood gas exchange has been attempted in the art. One known device consists of a plurality of small diameter gas permeable tubes connected to headers at each end. The headers are connected on one end to a source of oxygen rich gas and on the other end to an exhaust means. The apparatus is positioned within the vena cavae by means of a two-step process. First, an incision is made in the patient's femoral or iliac vein or internal jugular vein and in the patient's jugular vein. A radiopaque guide catheter is inserted into the jugular vein and is guided through the superior and inferior vena cavae using a fluoroscope, so as to exit through the incision in the femoral or iliac vein or internal jugular vein. Second, the device is attached to the guide catheter and is pulled into the vena cavae by withdrawing the guide catheter from the jugular vein.

While the method of inserting this extrapulmonary blood gas exchange device within a patient's vena cavae has been successfully demonstrated, still there are some drawbacks. First, the need for two incisions in the patient's venous system not only increases the complexity of the procedure but also subjects the patient to significant trauma and safety risk. In addition, the need to insert a guide catheter from the patient's jugular vein to the femoral or iliac vein or internal jugular vein exposes the patient to a serious risk of damaging the sensitive intimal tissues of the patient's venous system. Furthermore, the blood gas exchange device itself must have a small overall diameter to be able to pass through relatively narrow veins such as the jugular vein. As a result, when the device is within the vena cavae, which have a much larger diameter than the jugular vein, the blood flow bypasses the gas permeable tubes. Thus, blood contact with the surface of the gas permeable tubes is reduced.

In an attempt to avoid this problem, a spiral or undulating arrangement of the gas permeable tubes has been used. This increases the blood contact with the gas permeable tube surfaces. Also, the undulating or spiral arrangement of the gas permeable tubes reduces laminar blood flow through the vena cavae. Laminar blood flow is undesirable because such flow produces a boundary layer between the bulk flow of the blood and the surface of the gas permeable tubes. This boundary layer of blood significantly reduces gas transfer. The undulating or spiral arrangement of the gas permeable tubes offers limited improvement in performance of the device.

Recently, an in vivo extrapulmonary blood exchange device has been developed which is described in U.S. Pat. No. 4,850,958, entitled "Apparatus and Method for Extrapulmonary Blood Gas Exchange," issued Jul. 25, 1989. That device has a bundle comprising a plurality of gas permeable tubes bound at each end and enclosed within air tight proximal and distal chambers. The device also has a dual lumen tube with an outer lumen and an inner lumen which is situated relative to the gas permeable tubes such that the outer lumen terminates within the proximal chamber and such that the inner lumen terminates within the distal chamber. The outside diameter of the bundle of gas permeable tubes may be selectively adjusted to provide either a furled, small insertion diameter when inserting the apparatus into the vena cavae of a patient or an unfurled, expanded oxygenation diameter after the apparatus is in place within the vena cavae and the bundle of gas permeable tubes is deployed therein. Because the device is typically inserted into the patient through a single incision at one of the right external iliac, common femoral or internal jugular veins, care must be taken not to damage the delicate gas permeable tubes or the sensitive intimal tissues of the patient's venous system.

Over the years, sheaths and obturators have been used to assist in introducing various types of medical devices into a patient's body. Always, a major concern is the damage caused to the tissue surrounding the invasive path of the sheath, obturator, or medical device. An additional concern is the delicate handling of the medical device to avoid damage to the device which may inhibit its effectiveness. In inserting the particularly delicate in vivo blood gas exchange device referenced above, care must be taken not to snag, pinch, crush, or kink the gas permeable tubes. Sheaths and obturators which are known in the art are not suited to solve or minimize these concerns.

BRIEF SUMMARY AND OBJECTS OF THE INVENTION

The present invention seeks to resolve problems incident to the insertion of particularly sensitive medical devices such as an extrapulmonary blood gas exchange device into a patient's venous system. More specifically, the apparatus and method of this invention constitute an important advance in the art of inserting in vivo extrapulmonary blood gas exchange devices and other devices requiring delicate insertion, as evidenced by the following objects and advantages realized by the invention over the prior art.

One object of the present invention is to provide an apparatus and method for insertion of an in vivo extrapulmonary blood gas exchange device into a patient's venous system with minimal damage to sensitive intimal tissues.

Additionally, it is an object of the present invention to provide an apparatus for receiving for passage therethrough an in vivo extrapulmonary blood gas exchange device which avoids snagging, kinking, or crushing delicate gas permeable tubes and assists in compressing such tubes into a diameter conducive to smooth insertion into a patient's venous system.

Still an additional object of the present invention is to provide a sheath for receiving an in vivo extrapulmonary blood gas exchange apparatus or other device which is configured such that its receiving end may be disposed upwardly to more effectively inhibit loss of blood during use through the sheath and to collect a small reservoir of blood therein under hydrostatic pressure.

Another object of the present invention is to provide a sheath for receiving an obturator, an in vivo extrapulmonary blood exchange device or other device which has a smooth insertion path due to the configuration of the sheath so that snagging or binding of the device being inserted are avoided.

Still a further object of the present invention is to provide an obturator which facilitates the insertion of the sheath into a patient's venous system and which has a venting means which enables blood flow, under hydrostatic pressure through a portion of the obturator into the sheath thereby reducing suction upon its removal and further reducing the risk of introducing an air embolism into the blood stream of the patient.

Additional objects and advantages of the invention will be apparent from the description which follows, or may be learned by the practice of the invention.

Briefly summarized, the foregoing objects and advantages are realized by the apparatus and method of the present invention, which are designed for use on a routine basis and can be used with the surgical procedures mentioned herein or with other procedures requiring the introduction of a medical device into a patient's venous system. Particularly, the apparatus and method of the present invention can be used to facilitate blood oxygenation by assisting in the insertion of an in vivo extrapulmonary blood gas exchange device instead of the routine lung ventilation or the more invasive extracorporeal membrane oxygenation systems now used to treat patients with inadequate blood gas exchange.

In one embodiment of the present invention, the apparatus comprises a sheath and an obturator. The sheath has a hollow substantially tubular body with a receiving end and an entry end and an opening at each end. The opening at the receiving end is larger than the opening at the entry end and is configured to receive therethrough the obturator or a medical device such as an in vivo extrapulmonary blood gas exchange device. The opening at the entry end is configured to facilitate introduction of the sheath into the patient's venous system through an incision and the opening is just large enough to permit passage therethrough of a tip of the obturator or a medical device intended for insertion into the patient's venous system. The sheath, once inserted into the patient's venous system, serves to guide the medical device into the patient's venous system with a minimum of damage to the intimal tissue of the body.

The sheath is a unitary member with a portion tapered from the receiving end to the entry end (i.e., a transverse section in the tapered portion nearer the receiving end would have a larger diameter than a transverse section in the tapered portion farther from the receiving end), and throughout this specification the tapered portion of the sheath shall be referred to as the receiving portion. Another portion of the sheath is substantially nontapered or equidiametered (i.e., a transverse section in the nontapered portion of the sheath would have substantially the same diameter as any other transverse section in the nontapered portion of the sheath), and throughout this specification the nontapered portion of the sheath shall be referred to as the entry portion. The nontapered entry portion is configured with a curvature. The relationship of the receiving portion to the entry portion will be explained in more detail below.

The obturator comprises a rod-like elongate member with a tip connected thereto at one end and a grip connected thereto at the other end. The obturator closes the entry end of the sheath and adds stability to the sheath to facilitate the insertion of the sheath into a patient's venous system. The tip is relatively short in length to prevent binding of the obturator within the sheath and has a rounded blunt end which protrudes through the entry end of the sheath if the obturator is fully inserted into the sheath so that the obturator will not snag or catch on the intimal tissue. The tip also has a vent conduit which communicates at one end with space and at the other end with a vent channel in the elongate member. When the obturator is fully inserted into the sheath, the vent channel in the elongate member communicates with the interior space of the sheath thus providing a small capillary-like passageway from space exterior to the sheath at the tip of the obturator to the interior space of the sheath. This passageway permits the passage of a small amount of fluid to facilitate insertion of the sheath and extraction of the obturator from the sheath once it is positioned. The grip enables the user to grasp the obturator securely so that it can be inserted into or extracted from the sheath easily.

In anticipation of insertion of an extrapulmonary blood gas exchange device into a patient's venous system, the apparatus comprising the sheath with the obturator positioned fully therein is inserted into the patient through an incision made in either the common femoral vein, external iliac vein or the jugular vein. Upon insertion, the sheath is oriented so that the opening at the receiving end is disposed above the level of the incision so that when the obturator is removed, blood will not flow freely out of the sheath but will build under hydrostatic pressure a small reservoir of blood within the interior space of the sheath. The sheath is then in position to receive for insertion into the patient an extrapulmonary blood gas exchange device or some other medical device. If the device to be inserted is a blood gas exchange device as will be described in more detail below, the device is prepared before insertion. Preferably, the proximal chamber of the device is twisted relative to the distal chamber so that the gas permeable tubes are stretched and held tightly together reducing the overall diameter of the device to a diameter which is smaller than its untwisted diameter. During insertion, the gas permeable tubes are further compressed by the tapering of the interior wall of the sheath so that upon exiting the sheath the diameter of the blood gas exchange device is smaller than the interior diameter of the vein into which it is inserted. After insertion of the blood gas exchange device into the vena cavae, the proximal chamber is allowed to unwind so that the gas permeable tubes unfurl to fill the vena cavae.

The distal chamber preferably defines a short conduit formed therein which extends from a distal point on the distal chamber to a proximal point on the distal chamber. The conduit is oriented in a manner such that the conduit may be passed over a guidewire while the guidewire remains substantially exterior of the oxygenation apparatus. In this way, the apparatus may be inserted into the patient using a guidewire to direct the apparatus to the desired location. After insertion into the vena cavae, the guidewire is removed and the distal chamber is allowed to unwind so that the gas permeable tubes fill the vena cavae.

The distal chamber is twisted relative to the proximal chamber by means of a novel furling apparatus as described in the co-pending application entitled "Apparatus and Methods for Furling and Introducing an Extrapulmonary Blood Gas Exchange Device," Ser. No. 07/454,773 filed Dec. 22, 1989, and such description is included herein by this reference. The furling apparatus includes a device for removably engaging the proximal end of the inner lumen, a device for removably engaging the proximal end of the outer lumen, and a device for twisting the inner lumen relative to the outer lumen. Because the inner lumen is nonrotatably secured to the distal chamber, twisting the inner lumen simultaneously twists the distal chamber. Likewise, the outer lumen is nonrotatably secured to the proximal chamber. Thus, by twisting the inner lumen relative to the outer lumen, the distal chamber is twisted relative to the proximal chamber, and the gas permeable tubes are placed in either a twisted state, thereby forming an insertion diameter, or an untwisted state, thereby forming an oxygenation diameter.

The furling apparatus preferably includes a mechanism for indicating when the extrapulmonary oxygenation device is fully furled and fully unfurled. One embodiment providing this feature has a locking pin which automatically locks the furling apparatus when the device is furled and unfurled. Thus, in order to furl an unfurled device, the locking pin must be disengaged; likewise, in order to unfurl a furled device, the locking pin must be disengaged.

The furling apparatus also prevents sudden and undesired unfurling of the bundle of gas permeable tubes. This important advantage is achieved by preventing the furling apparatus from disengaging the inner lumen when the extrapulmonary oxygenation device is fully furled. One method for providing this feature is to retract the portion of apparatus which engages the proximal end of the inner lumen within the portion of the apparatus which twists the inner lumen, as the inner lumen is twisted. By the time the oxygenation device is fully furled, the device which releasably engages the inner lumen is not accessible for disengagement.

An important feature of the furling apparatus is the ability to removably insert a stylet within the inner lumen even when the gas permeable tubes are twisted into an insertion diameter. It has been found that the closer the distal end of the stylet gets to the distal chamber, the stiffer the distal end of the in vivo extrapulmonary oxygenation apparatus becomes. Thus, the rigidity of the apparatus may be adjusted, even during insertion, by sliding the stylet in or out of the inner lumen.

After the extrapulmonary oxygenation apparatus is inserted within the patient's venous system, the sheath is removed by withdrawing it from the incision and one of either the first or second lumens is connected to a source of oxygen rich gas. The other lumen is connected to an exhaust tube or other means for allowing the gas to flow out of the device. The oxygen rich gas flows into the gas permeable tubes. As venous blood flows around the gas permeable tubes, oxygen passes from the tubes into the blood causing blood oxygenation, and carbon dioxide passes from the blood into the tubes and out of the body. Gas flow through the tubes is augmented and risk of air embolism is eliminated by applying suction to the exhaust tube. The tubes are constructed of a material which allows efficient gas transfer yet is impervious to blood and is also relatively nonthrombogenic.

BRIEF DESCRIPTION OF THE DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only one or more typical embodiments of the invention and are therefore not to be considered limiting of its scope, the presently preferred embodiments and the presently understood best mode of the invention will be described with additional detail through use of the accompanying drawings in which:

FIG. 1 is a perspective view of one presently preferred embodiment of a sheath within the scope of the present invention showing a longitudinal center axis in dashed line;

FIG. 2 is a perspective view of one presently preferred embodiment of an obturator within the scope of the present invention;

FIG. 3 is a perspective view of an obturator fully disposed within a sheath showing that the tip of the obturator extends slightly beyond the entry end of the sheath and the grip abuts against the receiving end of the sheath;

FIG. 4 is an enlarged cut-away view of a portion of the embodiment illustrated in FIG. 3 taken with reference to line 4—4 showing the capillary-like passageway from space external to the sheath to space within the hollow interior of the sheath;

FIG. 5 is a perspective view of a patient showing the sheath and obturator inserted into a single incision in the patient's neck and showing a small reservoir of blood formed under hydrostatic pressure in the interior space of the sheath;

FIG. 6 is a perspective view of preferred embodiment of the sheath showing an extrapulmonary blood gas exchange device being inserted into the sheath and illustrating in an exaggerated fashion the compression of the gas permeable tubes.

DETAILED DESCRIPTION OF THE PREFERRED EMBODIMENTS

Reference is now made to the drawings wherein like parts are designated with like numerals throughout.

Referring first to FIG. 1, the sheath of the present invention, generally designated 10, is shown. The present invention comprises a sheath 10 for facilitating the insertion of a medical device into a patient's venous system, and more particularly, for facilitating the insertion of an extrapulmonary blood gas exchange device into a patient's venous system. The sheath 10 has a hollow substantially tubular member or body 12 having an interior wall 11 and an exterior wall 13. The sheath 10 also has a receiving end 14 and an entry end 16 with an opening at each end, a receiving opening 18 and an entry opening 20, respectively. The receiving opening 18 is larger than the entry opening 20 and is configured to receive therethrough the obturator or a medical device such as an in vivo extrapulmonary blood gas exchange device. The entry opening 20 is configured to facilitate introduction of the sheath 10 into the patient's venous system through an incision and the entry opening 20 is just large enough to permit passage therethrough of a tip of the obturator or a medical device intended for insertion into the patient's venous system.

The body 12 of the sheath 10 is unitary with a receiving portion, generally designated 22, tapered from the receiving end 14 towards the entry end 16 (i.e., a transverse section in the tapered receiving portion 22 nearer the receiving opening 18 would have a larger diameter than a transverse section in the receiving portion 22 farther from the receiving opening 18). The sheath 10 also has an entry portion, generally designated 24, which is substantially nontapered or equidiametered (i.e., a transverse section in the nontapered entry portion 24 of the sheath 10 would have substantially the same diameter as any other transverse section in the nontapered entry portion 24).

The entry portion 24 is configured with a curvature defined by a radius of curvature as drawn from a center of curvature (not shown) remote from the entry portion 24. For example, the preferred radius of curvature for a sheath 10 intended for use to facilitate the insertion of an extrapulmonary blood gas exchange device into a patient's venous system is in a range about five inches. With such a radius of curvature, the receiving portion 22 may be disposed such that the receiving opening 18 is oriented above the level of the entry opening 20 when the sheath 10 is inserted into a patient's venous system thereby preventing loss of blood and the curvature is sufficiently gentle and gradual to not subject the delicate gas permeable tubes of an extrapulmonary blood gas exchange device to excessive mechanical stress conditions. Of course, larger or smaller radiuses may be used without departing from the spirit of the present invention and depending upon the nature of the intended use of the sheath 10.

In a preferred embodiment of the sheath 10 of the present invention, the entry portion 24, at a point most remote from the receiving opening 18, has a bevelled edge 26 which encircles the entry opening 20. The bevelled edge 26 is the first part of the sheath 10 to encounter body tissue when being inserted into a patient's venous system, and is bevelled to reduce the likelihood that sensitive tissue will be snagged or traumatized during the insertion procedure. Also, the receiving portion 22, at a point most remote from the entry opening 20, has a flange 28 which encircles the receiving opening 18 and preferably curves outward from the longitudinal axis 30 of the sheath 10. The flange 28 serves an abutment against which the obturator grip or handle abuts to prevent insertion of the obturator too far into the sheath 10. Further, the flange 28 preferably curves outward to reduce the likelihood that the sheath 10 will snag, abrade or otherwise damage the delicate gas permeable tubes of an extrapulmonary gas exchange device or a medical device being inserted into and through the sheath 10. Although the bevelled edge 26 and flange 28 features of the present invention are preferred, it should be understood that these features are not necessary to the operation of the sheath 10 for its intended purpose. Also, it should be appreciated that the ends to the sheath 10 can be configured in a variety of ways in order to be adaptable to various uses and for facilitation of the receiving of a variety of medical devices of different sizes and shapes.

In a preferred embodiment, the receiving portion 22 adjoins the entry portion 24 at a juncture 32, designated in FIG. 1 by a dotted line. The juncture 32 represents where the tapering of the receiving portion 22 ends and the nontapering of the entry portion 24 begins. Since a smooth, snag-free interior wall 11 for the sheath 10 offers advantages in facilitating the insertion of an obturator or a medical device into and through the sheath 10, it is preferred that the interior wall 11 of the receiving portion 22 is in register with the interior wall 11 of the entry portion at the juncture 32 so that the interior wall 11 of the sheath 10 may have no corners or edges in order that the insertion path usually travelled along the interior wall 11 by the obturator or the medical device during the insertion procedure is free of obstructions.

It is important that the insertion path usually travelled along the interior wall 11 by an obturator or other medical device during the insertion procedure be smooth and free from obstructions. Due to the configuration of the preferred embodiment of the sheath 10, such path corresponds substantially to a line along the interior wall 11 defined by the intersection of the interior wall 11 and a plane (hereinafter referred to as the "longitudinal plane") defined by the longitudinal axis 30 and the center of the curvature (not shown) for the entry portion 24 of the sheath 10. Because the sheath 10 is tubular and hollow, the longitudinal plane so described intersects the interior wall 11 in two separate lines of intersection. The line of intersection which corresponds substantially to the path usually traveled is the line of intersection between the interior wall 11 and the longitudinal plane which is more remote from the center of curvature than the other line of intersection. Such line extends the entire length of the sheath 10 and shall hereinafter be referred to throughout this application and the appended claims as the "longitudinal surface base line." The longitudinal surface base line in the entry portion 24 substantially coincides to the arc of the same radius of curvature disposed in the longitudinal plane.

To avoid encountering corners, edges, or other obstructions along, at, or near the longitudinal surface base line during the insertion procedure, it is preferred that the sheath be configured with an arcual taper which is symmetrical about the longitudinal center axis. The preferred radius of curvature R (See FIG. 1) for the symmetrical flaring of the receiving portion 22 is in the range of about ninety-nine inches. Such a large radius of curvature is gradual and defines a taper which does not create a corner or edge at the juncture nor will it subject the delicate gas permeable tubes of an extrapulmonary blood gas exchange device to excessive mechanical stress conditions. The tangents of the arcual taper of the interior wall 11 of the sheath 10 taken at each point along the juncture 32 correspond substantially to the interior wall 11 within the entry portion 24 of the sheath 10 near the juncture 32. In this manner, the interior wall 11 has a smooth transition from the receiving portion 22 to the entry portion 24 at the juncture 32. Also, the tangent for the entry portion 24 lying in the longitudinal plane taken at the juncture 32 (Point T of FIG. 1) corresponds substantially to the tangent of the arcual taper of the receiving portion 22 at Point T.

Although it is preferred that the sheath 10 be configured with a symmetrical, arcual taper of the receiving portion 22, it should be understood that the tapering of the receiving portion 22 may be nonarcual and defined substantially by the tangent taken in the longitudinal plane at the juncture 32 or by other angles of tapering which still provide a relatively smooth insertion of an obturator or other medical device into the sheath 10. Further, such an angle of the tapering is somewhat dependent upon the radius of curvature of the entry portion 24, if a relatively smooth interior wall 11 is desired.

With reference now to FIG. 2, the obturator, generally designed 40, comprises a rod-like elongate member 42 with a tip 44 connected thereto at one end (the distal end) and a gripping means 46 connected thereto at the other end (the proximal end). The obturator 40 closes the entry end 16 of the sheath 10, adds stability to the sheath 10, and provides a blunt, atraumatic tip 44 to facilitate the insertion of the sheath 10 into a patient's venous system. The elongate member 42 preferably has a curvature consistent with the curvature of the entry portion 24 and is flexible so that upon insertion of the obturator 40 into the sheath 10 significant disfiguration of the sheath 10 is avoided.

The tip 44 is relatively short to prevent binding within the sheath 10 and has a rounded blunt, atraumatic end 48 which protrudes through the entry end 16 of the sheath 10 if the obturator 40 is fully inserted into the sheath 10 (as shown in FIG. 3) so that the obturator 40 will not snag or catch on the intimal tissue of the patient. In a preferred embodiment of the present invention, the curvature of the rounded blunt end 48 complements the bevel angle of the bevelled edge 26 of the entry portion 24 so that the tip 44 and the sheath 10 present a relatively snag-free surface.

It is further preferred that the tip 44 also has a vent conduit 50 which communicates at the rounded blunt end 48 with space exterior to the sheath 10 and at the other end with a vent channel 52 in the elongate member 42. When the obturator 40 is fully inserted into the sheath 10, the vent channel 52 in the elongate member 42 communicates with the interior space of the sheath 10 thus providing a small capillary-like passageway from space exterior to the sheath 10 at the tip 44 to the interior space of the sheath 10, as shown in FIG. 4. This passageway permits the passage of a small amount of fluid to facilitate insertion of the sheath 10 and extraction of the obturator 40 from the sheath 10 once it is positioned.

It should be understood that the tip 44 may be formed unitary with the elongate member 42 or it may be connected in some fashion such as by threaded engagement (See FIG. 4) or some other means. Certainly, if the tip 44 is removable from the elongate member 42, tips 44 of various sizes may be used interchangeably to correspond to sheaths 10 having various sized diameters at the entry opening 20.

The gripping means 46 enables the user to grasp the obturator 40 securely so that it can be inserted into or extracted from the sheath 10 easily. Likewise, the gripping means 46 may be formed unitary with the elongate member 42 or it may be connected in some fashion such as by threaded engagement or some other means. If the gripping means 46 is removable from the elongate member 42, elongate members 42 of various lengths may be used interchangeably to correspond to sheaths 10 having various lengths. Preferably, the gripping means 46 also comprises a stop 54 which engages the receiving portion 22 in a seated engagement which restricts further insertion of the obturator 40 into the sheath 10.

By way of example and with reference now to FIGS. 5 and 6, the insertion of an extrapulmonary blood gas exchange device into a patient will be described; however, it should be understood that the sheath 10 and obturator 40 may be used to facilitate the insertion of many other types of medical devices into a patient's venous system. The apparatus comprising the sheath 10 with the obturator 40 positioned fully therein (as shown in FIG. 3) is inserted into a patient 60 through a single incision 62. The incision 62 may be made in either the common femoral vein, external iliac vein or internal jugular vein. As shown in FIG. 5, the incision 62 is made to access the jugular vein.

Upon insertion, the sheath 10 is oriented so that the receiving opening 18 is disposed above the level of the incision 62 so that when the obturator 40 is removed blood will not flow freely out of the sheath 10 but will build under hydrostatic pressure a small reservoir 64 of blood within the interior space of the sheath 10. Hence, if the patient 60 is lying substantially horizontal, the receiving portion 22 of the sheath 10 is disposed upward at an angle from the horizontal, as illustrated in FIG. 5. The sheath 10 is then in position for the extraction of the obturator 40 and to receive the insertion of an extrapulmonary blood gas exchange device or some other medical device into the patient 60. If the device to be inserted is a blood gas exchange device of a type described above, it is prepared before insertion.

Referring now to FIG. 6, an extrapulmonary blood gas exchange device or oxygenator 70 includes a plurality of elongated gas permeable tubes 72 which are bundled together. Gas permeable tubes 72 each have a proximal end 74 and a distal end 76. Both the proximal ends and the distal ends of the gas permeable tubes 72 are bound tightly together to form cylindrical ends. The blood gas exchange device 70 is advantageously comprised of a tube means comprising first and second lumens, one of which extends the length of the gas permeable tubes 72, such that one of the lumens terminates adjacent the distal ends 76 of tubes 72, while the other lumen terminates adjacent the proximal ends 74 of tubes 72. This tube means with the first and second lumens eliminates the need for two incisions, rendering insertion into the vena cavae much easier and less traumatic. Means are provided for introducing oxygen from the first lumen into the gas permeable tubes 72, and another means is provided for collecting carbon dioxide as it exits the gas permeable tubes 72 and introducing the carbon dioxide into the second lumen for removal from the blood gas exchange device 70.

One way of providing the functions of introducing oxygen into the gas permeable tubes 72 and thereafter collecting carbon dioxide as it exits the gas permeable tubes 72 is achieved by a means for enclosing the proximal and distal ends 74 and 76 of the gas permeable tubes 72 to form airtight chambers. The proximal ends 74 of the gas permeable tubes 72 are disposed within a proximal chamber 78 which also encloses the distal end of an outer lumen. The proximal chamber 78 is airtight such that the outer lumen is in gaseous communication with the bound proximal ends 74 of the gas permeable tubes 72. Similarly, the distal ends 76 of gas permeable tubes 72 are disposed within a distal chamber 80 which also encloses the distal end of an inner lumen. The distal chamber 80 is airtight such that the potted distal ends 76 of the gas permeable tubes 72 are in gaseous communication with the inner lumen.

The gas exchange device 70 is designed for in vivo extrapulmonary blood gas exchange within the vena cavae of a patient. The particulars of what components comprise the device and how it functions are set forth in U.S. Pat. No. 4,850,958 and are incorporated herein by this reference.

To use the device 70 in vivo, it should preferably have an overall outside diameter with respect to the bundle of gas permeable tubes 72 that is sufficiently small to be inserted within the vena cavae through a peripheral vein, yet also have an overall outside diameter of the bundle that is sufficiently large to fill the vena cavae cross-section once tubes 72 are deployed therein. To achieve both of these objectives, the overall diameter of the gas permeable tubes 72 may be selectively adjusted to provide either a small insertion diameter when inserting the apparatus within the vena cavae or an expanded oxygenation diameter after the apparatus is in place within the vena cavae.

To selectively adjust the overall outside diameter of the bundle of gas permeable tubes 72, the gas permeable tubes are twisted and elongated. The overall outside diameter of the bundle of gas permeable tubes 72 is adjusted by twisting either the proximal chamber 78 or the distal chamber 80 relative to the other. After the gas permeable tubes 72 have been tightly twisted and elongated, a locking ring permits the gas permeable tubes 72 to remain twisted and elongated while the apparatus is inserted into the patient. As shown in FIG. 6, the diameter of the tightly twisted gas permeable tubes 72 is shown near the entry end 16. This diameter represents an insertion diameter sufficiently small to enable the apparatus to be inserted within the vena cavae through a small peripheral vein. For illustrative purposes, the diameter of the gas permeable tubes 72 shown near the receiving end 14 shows a diameter possible within the vena cavae when the gas permeable tubes 72 are untwisted. After insertion within the vena cavae of the patient, the locking ring may be released so that the gas permeable tubes 72 may be untwisted.

Reference is now made to FIGS. 5 and 6 wherein the method of using the present invention is illustrated. FIG. 5 specifically illustrates the placement of the present invention within a patient 60. As can be seen in FIG. 5, the sheath 10 with the obturator 40 positioned therein is inserted through a single incision 62 into the jugular vein. It should be understood that insertion can also be accomplished through single incisions into other veins such as the right external iliac or the right femoral vein. During insertion, the pressure imposed on the venous system of the patient 60 is minimized because blood is permitted to flow through the passageway defined by the vent conduit 50 and the vent channel 52 and allowed to pool within the sheath 10 at reservoir 64. Once positioned, the obturator 40 is extracted from the sheath 10. The suction that would otherwise occur during the extraction process is significantly reduced due to the fact that blood or air from the reservoir 64 can pass through the passageway defined by the vent channel 52 and the vent conduit 50.

Prior to insertion of the blood gas exchange device 70 into the vena cavae as guided by the sheath 10, the overall diameter of the bundle of gas permeable tubes 72 is reduced by twisting and by further compression as best illustrated in FIG. 6. Although the compression shown in FIG. 6 is exaggerated, it does illustrate the compressing function of the receiving portion 22 of the sheath 10.

For safety reasons it is important to hydrate the gas permeable tubes 72 and to remove any air bubbles which might remain between the individual tubes prior to inserting the device within the vena cavae. It is also very important that the gas permeable tubes 72 not be snagged, kinked, or crushed during insertion. Thus, the gradual tapering of the receiving portion 22 of the sheath 10 serves the dual role of compression and avoiding snagging, kinking, and crushing.

Once the blood gas exchange device 70 is in place, it may be connected to a source of oxygen-enriched gas and to a vacuum or some other exhaust means. As a result, oxygen-enriched gas will travel through the gas permeable tubes 72. During the time the oxygen-enriched gas is within the gas permeable tubes 72 it will be able to oxygenate the blood traveling through the vena cavae. In addition, carbon dioxide is enabled to pass from the blood into the gas permeable tubes 72 and thereby be removed from the blood stream. Oxygen and carbon dioxide can readily travel through the walls of gas permeable tubes 72, but blood cannot enter the tubes 72. Thus, oxygenation can occur without the blood being directly exposed to gas bubbles.

In summary, the method and apparatus disclosed herein is a significant advance in facilitating the insertion of medical devices into the human venous system. Also, the method and apparatus of the present invention particularly facilitates a significant departure from the traditional extrapulmonary blood gas exchange systems of the prior art. In the present invention, only a single venous incision is required for inserting a medical device such as an extrapulmonary blood gas exchange device within the patient's venous system. With regard to insertion of an in vivo extrapulmonary blood gas exchange device, oxygen is added to and carbon dioxide is removed from circulating blood without molesting, forcing, or irritating ailing or diseased lungs. In addition, the overall outside diameter of the blood gas exchange device may be adjusted to have a narrow diameter for insertion within the patient or adjusted to have an expanded diameter during blood oxygenation. As a result, blood surface contact with the gas permeable tubes is maximized, laminar blood flow through the vena cavae is inhibited and disturbed flow of blood over the tubes is achieved, thereby providing efficient blood gas exchange.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A sheath for receiving an obturator in sliding engagement, comprising:
   a hollow substantially tubular member having a receiving end and an entry end;
   a receiving opening at the receiving end;
   an entry opening at the entry end, at least a portion of said tubular member being substantially tapered from the receiving end towards the entry end, whereby said entry opening is smaller than said receiving opening; and
   a receiving portion adjacent the receiving end and an entry portion adjacent the entry end, said entry portion being non-tapered and having a substantially uniform arcuate curve defined by a substantially uniform radius of curvature, and said receiving portion having a substantially uniform arcuate taper from said receiving opening to a juncture where said receiving portion adjoins said entry portion, and said receiving portion adjoining said entry portion at said juncture at an angle corresponding to a tangent to said arcuate curve so as to define a continuous path of entry through said hollow member that is free of corners and edges.

2. A sheath as set forth in claim 1, wherein said taper of said receiving portion is symmetrical about the longitudinal axis of said receiving portion.

3. A sheath as set forth in claim 1, wherein the curvature of said entry portion is configured such that a longitudinal surface base line of said entry portion is disposed in a plane defined by the center of curvature and a longitudinal axis of said entry portion and the longitudinal surface base line substantially coincides with the arc of the same radius of curvature disposed in the plane; and wherein a longitudinal surface base line of said receiving portion is disposed within the plane and substantially corresponds to a segment of the tangent to the arc taken at the juncture, whereby the longitudinal surface base line of said receiving portion and the longitudinal axis of said receiving portion define substantially the angle of taper of said receiving portion.

4. A sheath as set forth in claim 1, wherein said tubular member further comprises a bevelled edge encircling said entry opening.

5. A sheath as set forth in claim 1, wherein said tubular member further comprises a flange encircling said receiving opening.

6. An sheath as set forth in claim 5, wherein said flange curves outward from the longitudinal axis of said tubular member.

7. An apparatus comprising in combination:
   an obturator;
   a sheath for receiving said obturator in sliding engagement, said sheath comprising:
      a hollow substantially tubular member having a receiving end and an entry end;
      a receiving opening at the receiving end;
      an entry opening at the entry end, at least a portion of said tubular member being substantially tapered from the receiving end towards the entry end whereby said entry opening is smaller than said receiving opening; and
      a receiving portion adjacent the receiving end and an entry portion adjacent the entry end, said entry portion being non-tapered and having a substantially uniform arcuate curve defined by a substantially uniform radius of curvature, and said receiving portion having a substantially uniform arcuate taper from said receiving opening to a juncture where said receiving portion adjoins said entry portion, and said receiving portion adjoining said entry portion at said juncture at an angle corresponding to a tangent to said arcuate curve so as to define a continuous path of entry through said hollow member that is free of corners and edges.

8. An apparatus as set forth in claim 7, wherein said obturator is configured with a curvature.

9. An apparatus as set forth in claim 8, wherein the curvature of said entry portion is configured such that a longitudinal surface base line of said entry portion is disposed in a plane defined by the center of curvature and a longitudinal axis of said entry portion and the longitudinal surface base line substantially coincides with the arc of the same radius of curvature disposed in the plane; and wherein a longitudinal surface base line of said receiving portion is disposed within the lane and substantially corresponds to a segment of the tangent to the arc taken at the juncture, whereby the longitudinal surface base line of said receiving portion and the longitudinal axis of said receiving portion substantially define the angle of taper of said receiving portion.

10. An apparatus as set forth in claim 7, wherein the taper of said receiving portion is symmetrical about the longitudinal axis of said receiving portion.

11. An apparatus as set forth in claim 7, wherein said tubular member further comprises a bevelled edge encircling said entry opening.

12. An apparatus as set forth in claim 11, wherein said obturator further comprises a tip with a rounded blunt end; said tip protrudes partially through and closes said entry opening if said obturator is inserted fully within said sheath from the receiving end thereof; and wherein said bevelled edge is disposed at an angle from the longitudinal axis of said entry portion such that when said obturator is inserted fully within said sheath a substantially snag-free outer surface results proximate to said entry opening.

13. An apparatus as set forth in claim 7, wherein said tubular member further comprises a flange encircling said receiving opening.

14. An apparatus as set forth in claim 13, wherein said flange curves outward from the longitudinal axis of said tubular member.

15. An apparatus as set forth in claim 7, wherein said obturator comprises a tip; said tip protrudes through and closes said entry opening if said obturator is inserted fully within said sheath from the receiving end thereof.

16. An apparatus as set forth in claim 15, wherein said obturator further comprises:
an elongate member; and
means for connecting detachably said tip to said elongate member.

17. An apparatus as set forth in claim 16, wherein said means for connecting detachably said tip to said elongate member comprises cooperating threads on said tip and on the distal end of said elongate member.

18. An apparatus as set forth in claim 16, wherein said means for connecting detachably said tip to said elongate member is capable of connecting a plurality of tips of various sizes, said tips being connectable interchangeably to said elongate member.

19. An apparatus as set forth in claim 16, wherein formed through said tip is a vent conduit communicates at one end thereof with space when said obturator is fully inserted within said sheath, and formed in said elongate member is a vent channel which communicates between said vent conduit and atmosphere, said vent conduit and said vent channel permitting the flow of fluid through said vent conduit and said vent channel into the hollow interior of said sheath if said tip encounters a fluid while said obturator is inserted fully within said sheath.

20. An apparatus as set forth in claim 16, wherein said elongate member is flexible.

21. An apparatus as set forth in claim 16, wherein said obturator further comprises:
a gripping means; and
a means for connecting detachably said gripping means to said elongate member.

22. An apparatus as set forth in claim 21, wherein said means for connecting is capable of connecting a plurality of elongate members of various lengths, said elongate members being connectable interchangeably to said gripping means.

23. An apparatus as set forth in claim 21, wherein said means for connecting detachably said gripping means to said elongate member comprises cooperating threads on said gripping means and on the proximal end of said elongate member.

24. An apparatus as set forth in claim 21, wherein said gripping means comprises a stop which engages the receiving end of said tubular member to restrict further insertion of said obturator into said sheath 25. An apparatus as set forth in claim 24, wherein said tubular member further comprises a flange encircling said receiving opening which engages said stop to restrict further insertion of said obturator into said sheath.

26. An apparatus as set forth in claim 25, wherein said flange curves outward from the longitudinal axis of said tubular member.

27. An apparatus for facilitating the introduction of an extrapulmonary blood exchange device into the vena cavae of a patient, comprising:
an obturator;
a sheath for receiving said obturator in sliding engagement, said sheath comprising:
a hollow substantially tubular member having a receiving end and an entry end; said entry end for introduction into a vein of the patient;
a receiving opening at the receiving end;
an entry opening at the entry end, at least a portion of said tubular member being substantially tapered from the receiving end towards the entry end whereby said entry opening is smaller than said receiving opening; said entry opening is capable of permitting passage of the blood gas exchange device therethrough and into the vena cavae; and
a receiving portion adjacent the receiving end and an entry portion adjacent the entry end, said entry portion being non-tapered and having a substantially uniform arcuate curve defined by a substantially uniform radius of curvature, and said receiving portion having a substantially uniform arcuate taper from said receiving opening to a juncture where said receiving portion adjoins said entry portion, and said receiving portion adjoining said entry portion at said juncture at an angle corresponding to a tangent to said arcuate curve so as to define a continuous path of entry through said hollow member that is free of corners and edges.

28. An apparatus as set forth in claim 27, wherein said taper of the receiving portion is symmetrical about the longitudinal axis of said receiving portion.

29. An apparatus as set forth in claim 27, wherein said entry portion is configured with a curvature such that upon insertion of said entry end of said sheath into the vein of the patient lying substantially horizontal said entry portion is capable of disposition such that said receiving portion is disposed upward at an angle from the horizontal.

30. An apparatus as set forth in claim 2, wherein the curvature of said entry portion is configured such that a longitudinal surface base line of said entry portion is disposed in a plane defined by the center of curvature and a longitudinal axis of said entry portion and the longitudinal surface base line substantially coincides with the arc of the same radius of curvature disposed in the plane; and wherein a longitudinal surface base line of said receiving portion is disposed within the plane and substantially corresponds to a segment of the tangent to the arc taken at the juncture, whereby the longitudinal surface base line of said receiving portion and the longitudinal axis of said receiving portion define substantially the angle of taper of said receiving portion.

31. An apparatus as set forth in claim 30, wherein said tubular member further comprises a bevelled edge encircling said entry opening for reducing the snagging of the patient's body tissue upon insertion of said sheath into the patient;.

32. An apparatus as set forth in claim 31, wherein said obturator further comprising a tip with a rounded blunt end; said tip protrudes partially through and closes said entry opening if said obturator is inserted fully within said sheath from the receiving end thereof; and wherein said bevelled edge is disposed at an angle from the longitudinal axis of said entry portion such that when said obturator is inserted fully within said sheath a substantially snag-free outer surface results proximate to said entry opening whereby snagging of the patient's body tissue upon insertion into the vein is reduced.

33. An apparatus as set forth in claim 32, wherein formed through said tip is a vent conduit which communicates at one end thereof with space when said obturator is fully inserted within said sheath, and formed in said elongate member is a vent channel which communicates between said vent conduit and atmosphere, and upon insertion of said sheath with said obturator disposed therein into the vein of the patient, said vent conduit and said vent channel permit the flow of the patient's blood through said vent conduit and said vent channel into the hollow interior of said sheath.

34. An apparatus as set forth in claim 27, wherein said tubular member further comprises a flange encircling said receiving opening.

35. An apparatus as set forth in claim 34, wherein said flange curves outward from the longitudinal axis of said tubular member to reduce snagging of the blood gas exchange device on the receiving end of said sheath.

36. An apparatus as set forth in claim 27, wherein said obturator further comprises a tip which protrudes through and closes said entry opening if said obturator is inserted fully within said sheath from the receiving end thereof.

37. An apparatus as set forth in claim 36, wherein said obturator further comprises:
an elongate member; and
means for connecting detachably said tip to said elongate member.

38. An apparatus as set forth in claim 37, wherein said means for connecting detachably said tip to said elongate member comprises cooperating threads on said tip and on the distal end of said elongate member.

39. An apparatus as set forth in claim 37, wherein said means for connecting detachably said tip to said elongate member is capable of connecting a plurality of tips of various sizes, said tips being connectable interchangeably to said elongate member.

40. An apparatus as set forth in claim 37, wherein said elongate member is flexible.

41. An apparatus as set forth in claim 37, wherein said obturator further comprises:
a gripping means; and
means for connecting detachably said gripping means to said elongate member.

42. An apparatus as set forth in claim 41, wherein said means for connecting detachably said gripping means to said elongate member is capable of connecting a plurality of elongate members of various lengths, said elongate members being connectable interchangeably to said gripping means.

43. An apparatus as set forth in claim 41, wherein said means for connecting detachably said gripping means to said elongate member comprises cooperating threads on said gripping means and on the proximal end of said elongate member.

44. An apparatus as set forth in claim 41, wherein said gripping means comprises a stop which engages the receiving end of said tubular member to restrict further insertion of said obturator into said sheath.

45. An apparatus as set forth in claim 44, wherein said tubular member further comprises a flange encircling said receiving opening which engages said stop to restrict further insertion of said obturator into said sheath.

46. An apparatus as set forth in claim 45, wherein said flange curves outward from the longitudinal axis of said tubular member.

47. A method for inserting a medical device into a patient's venous system comprising the steps of:
preparing the patient by making a single incision access into the patient's venous system;
inserting an obturator into a hollow substantially tubular sheath with a receiving end and an entry end, said sheath comprising a receiving opening at the receiving end and an entry opening at the entry end, at least a portion of said sheath being substantially tapered from the receiving end towards the entry end, whereby said entry opening is smaller than said receiving opening;
positioning said obturator within said sheath such that a tip at the distal end of said obturator protrudes through said entry opening thereby closing said entry opening;
inserting said tip of said obturator and the entry end of said sheath through the incision into the venous system of the patient;
extracting said obturator from said sheath;
inserting the medical device into and through said sheath and into said venous system; and
wherein said sheath further comprises a receiving portion adjacent the receiving end and an entry portion adjacent the entry end and adjoined to the receiving portion, and said receiving portion is substantially tapered from the receiving end to said entry portion and said entry portion is substantially non-tapered and is configured with a curvature, said method further comprising the step of orienting the receiving portion of the sheath at an angle upward from the horizontal.

48. A method as set forth in claim 47, wherein said obturator has vent conduit which communicates with space exterior to said sheath and with the hollow interior space of said sheath, said method further comprising the step of permitting the patient's blood to flow through said vent conduit.

49. A method as set forth in claim 47, wherein said medical device is an extrapulmonary blood gas exchange device with a bundle of elongated gas permeable tubes, said method further comprising the step of compressing said elongated gas permeable tubes into a diameter sufficiently small to pass into the patient's venous system as the elongated gas permeable tubes exit from said sheath.

* * * * *

UNITED STATES PATENT AND TRADEMARK OFFICE
CERTIFICATE OF CORRECTION

PATENT NO. : 5,125,902

DATED : June 30, 1992

INVENTOR(S) : GAYLORD L. BERRY et al.

It is certified that error appears in the above-identified patent and that said Letters Patent is hereby corrected as shown below:

```
    Title page, column 1, "Assignee:  CardioPulmonics, Inc." should be
--Assignee:  Cardiopulmonics, Inc.--
    Abstract, line 12, "trip" should be --tip--
    Abstract, line 22, "a" should be --an--
    Column 8, line 35, after "serves" insert --as--
    Column 14, line 55, "lane" should be --plane--
    Column 15, line 35, after "conduit" insert --which--
    Column 16, line 66, delete ";"
    Column 16, line 68, "comprising" should be --comprises--
    Column 18, line 48, after "has" insert --a--
```

Signed and Sealed this

Twenty-third Day of February, 1993

*Attest:*

STEPHEN G. KUNIN

*Attesting Officer*     Acting Commissioner of Patents and Trademarks